US00PP36048P2

(12) United States Plant Patent
Van Swieten

(10) Patent No.: US PP36,048 P2
(45) Date of Patent: Jul. 30, 2024

(54) ***PHALAENOPSIS* ORCHID PLANT NAMED 'PHA882884'**

(50) Latin Name: ***Phalaenopsis* hybrid**
Varietal Denomination: PHA882884

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,754

(22) Filed: Jan. 17, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP35,476 P2 * 11/2023 Van Swieten ..... A01H 6/62
Plt./311

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHA882884', particularly characterized by having numerous white, flecked and striped flowers with extra-large, flecked and striped lips, flat flowers in lateral view, and is propagated by meristem tissue culture, is disclosed.

3 Drawing Sheets

Genus and species: *Phalaenopsis* hybrid.
Variety denomination: 'PHA882884'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA882884'.

The new *Phalaenopsis* plant is a product of a planned breeding program conducted by the inventor in Bleiswijk, the Netherlands. The objective of this breeding program was to create a new *Phalaenopsis* plant with numerous white, flecked and shaded flowers with extra-large, striped and flecked lips suitable for potted plant production.

The new *Phalaenopsis* plant 'PHA882884' is a result of cross-pollination made by the inventor in May 2016 in Bleiswijk, the Netherlands, of the proprietary female, or seed parent, *Phalaenopsis* hybrid '06240-0002' (unpatented) with the proprietary male, or pollen parent, *Phalaenopsis* hybrid '07-1-9269' (unpatented).

The new *Phalaenopsis* was selected by the inventor as a single plant within the progeny of the stated cross-pollination in a controlled greenhouse in Bleiswijk, the Netherlands, in February 2019. Asexual reproduction of the new *Phalaenopsis* plant by meristem tissue culture since 2020 in Bleiswijk, the Netherlands, has demonstrated that the new variety reproduces true to type with all the characteristics, as herein described, firmly fixed and retained through successive generations.

Community Plant Variety Rights for this variety have been applied for in the European Union on Jan. 22, 2023 (Application no. 2023/0212), by Applicant who obtained the subject matter disclosed directly from the inventor. 'PHA882884' has not been made publicly available or sold anywhere in the world prior to the effective filing date of this application with the exception of sales or disclosures made one year or less before the effective filing date of this claimed invention by Applicant who obtained 'PHA882884' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA882884' as a new and distinct variety of *Phalaenopsis* plant:

1) White, flecked and striped flowers with extra-large, flecked and striped lips;
2) flower shape in lateral view is flat; and
3) lip: callus is flecked.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2023. Colors in the photographs may differ from the color values cited in the detailed botanical description, which accurately describe the actual colors of the new variety.

DESCRIPTION OF THE NEW VARIETY

Figure 1:
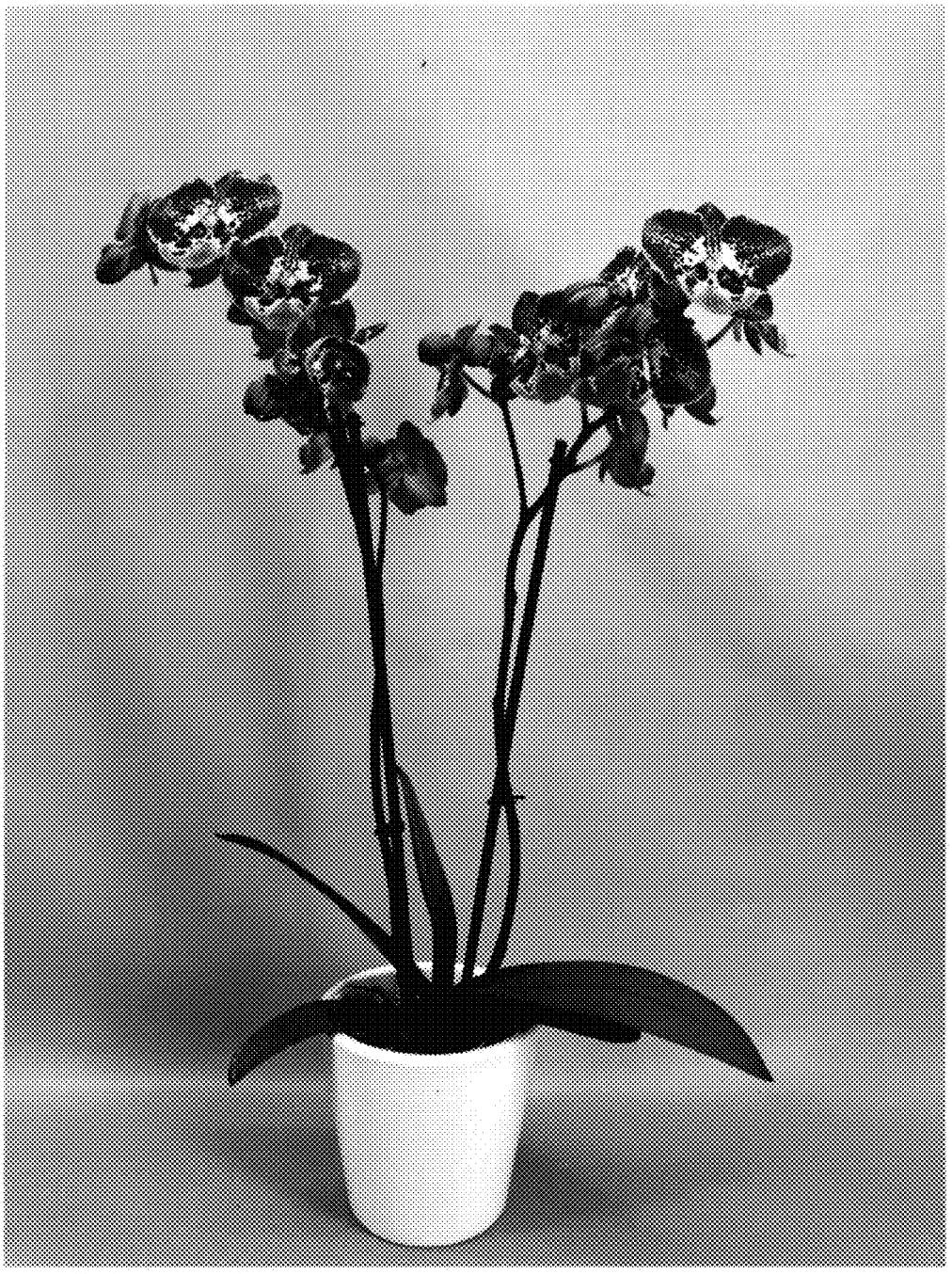
FIG. 1 shows the overall plant habit, including blooms, buds, and foliage of 'PHA882884'.
Figure 2:
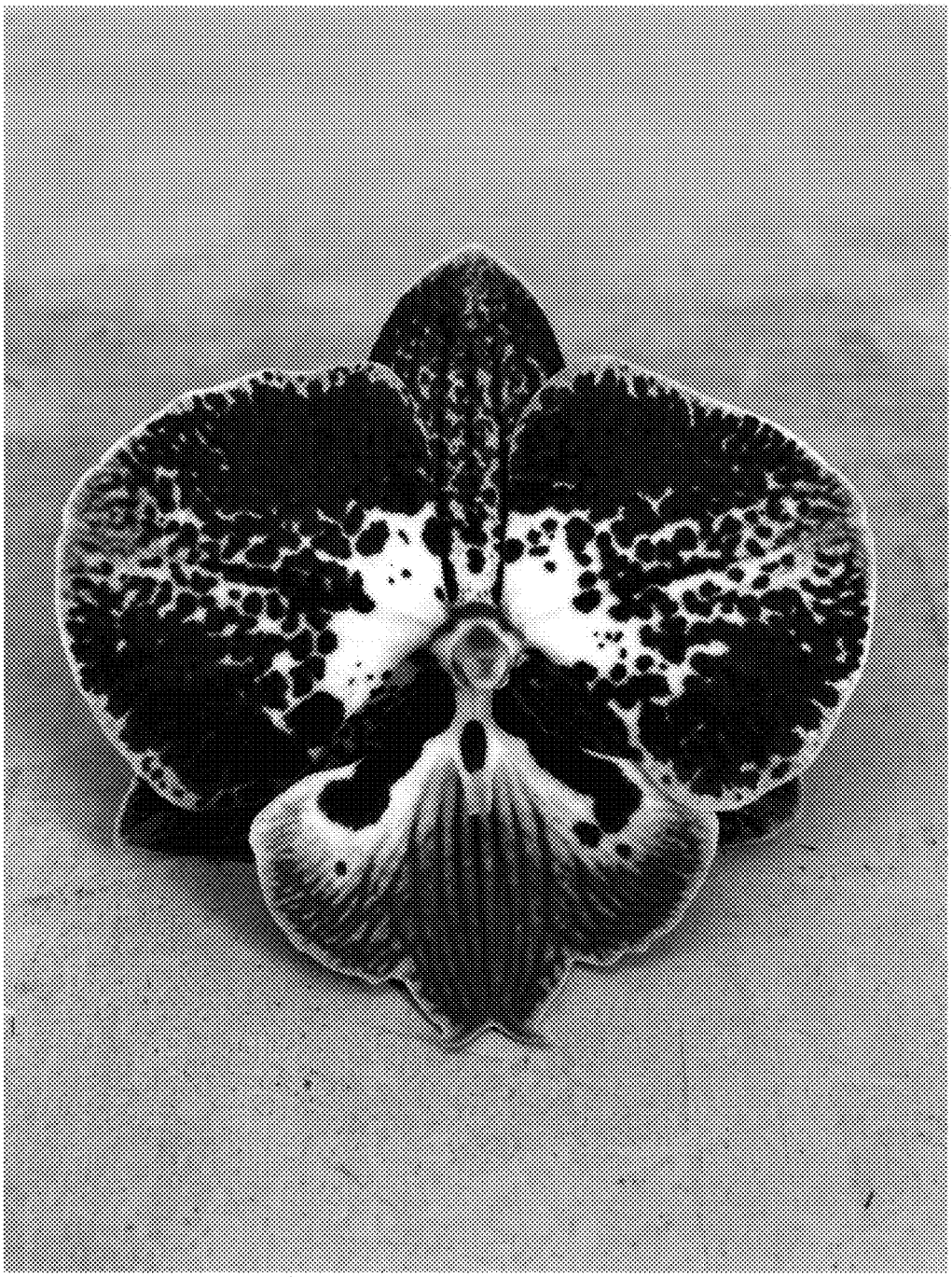
FIG. 2 shows a close-up of a flower of 'PHA882884'.
Figure 3:
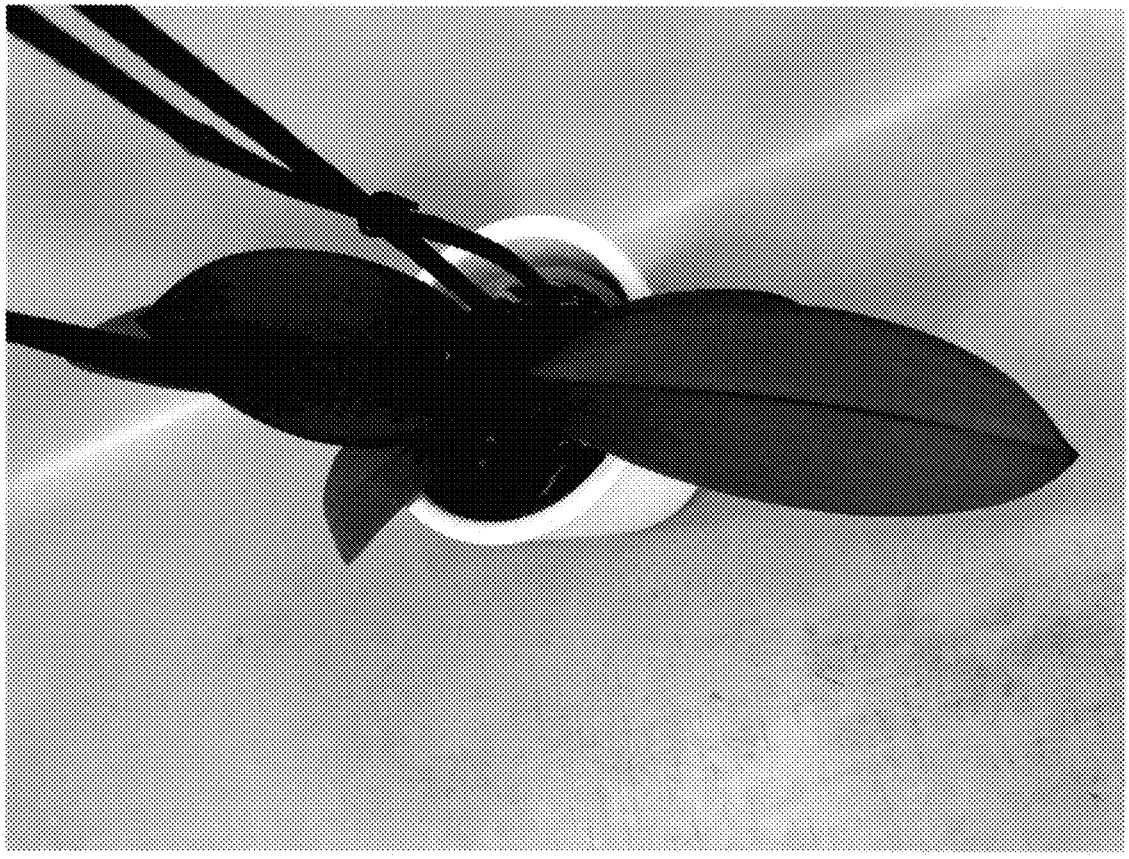
FIG. 3 shows an overhead, close-up view of the leaves of 'PHA882884'.

The following detailed description sets forth the distinctive characteristics of 'PHA882884'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA882884'.

Parentage:

*Female parent*.—*Phalaenopsis* cultivar '06240-0002' (unpatented).

*Male parent*.—*Phalaenopsis* cultivar '07-1-9269' (unpatented).

Propagation:

*Type*.—Meristem tissue culture.

Roots:

*Root description*.—Greyed-green colored roots (a color in between RHS 190B and RHS 190C) with branching lateral roots having small, greenish-yellow (RHS 151B) with a touch of purplish-red colored root tips (RHS N77B).

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 50.0 cm to 55.0 cm.

*Width* (*measured from leaf tips*).—About 38.0 cm to 40.0 cm.

*Vigor*.—Strong.

Leaves:

*Mature leaves*.—Quantity per plant: 7 to 8 leaves are produced before flowering. Length (fully expanded): 19.0 cm to 22.0 cm. Width: 6.0 cm to 7.0 cm. Position of the broadest part of the leaf: At the middle. Shape: Oblong. Base shape: Moderately elongated. Apex: Acute, moderately asymmetric. Leaf blade angle with the petiole (measured from the horizontal position): Between 15 degrees and 25 degrees. Leaf margin: Entire. Color: Upper surface: Green (RHS 146A) with dark red margin (RHS 187B). Lower surface: Green (RHS 146B) and dark red towards margins (RHS N186C). Texture (both upper and lower surfaces): Smooth. Thickness: 2.0 mm to 3.0 mm. Variegation: Absent. Venation: Pattern: Parallel. Color of the midvein: Upper surface: Green (RHS 146A). Lower surface: Purplish-red (RHS N77B).

Peduncle:

*Quantity per plant*.—2.

*Number of flowers per peduncle*.—13 to 16.

*Length*.—50.0 cm to 55.0 cm.

*Diameter*.—5.0 mm to 6.0 mm.

*Strength*.—Strong.

*Aspect*.—Upright to slightly pendent.

*Texture*.—Smooth.

*Color*.—Mix of brown (RHS 200A) and green (RHS 146C).

*Internode length*.—3.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip) 230.0 mm to 260.0 mm.

*Flowering time*.—First flowers can be expected 10 to 11 months after planting in a 12-cm pot.

*Flower*.—Height: 75.0 mm to 80.0 mm. Diameter: 80.0 mm to 85.0 mm. Depth of lip: About 2.0 mm.

*Flower shape*.—Flat.

*Flower longevity*.—On the plant: 9 to 11 weeks.

*Fragrance*.—Absent.

*Flower bud*.—Average size: Medium to large. Length: 27.0 mm to 29.0 mm. Width: 17.0 mm to 19.0 mm. Shape: Egg shaped. Color: Light yellow-green (RHS 145C) with purplish-red shade (RHS N77B) and dark purplish midveins (RHS N79C).

*Petals*.—Arrangement: Open/free. Shape: Moderately compressed to medium. Apex: Emarginated asymmetric. Margin: Entire. Length (from base to tip): 38.0 mm to 40.0 mm. Width: 47.0 mm to 49.0 mm. Position of the broadest part of the petal: Toward the base. Color (when fully opened): Upper surface: Basic color: White (RHS NN155C). Over color: Light purple shade (RHS 76A) toward margins; reddish-purple flecks (RHS N78A); purplish-pink (RHS N78C) with netting RHS N78B toward apex. Lower surface: Basic color: White (RHS NN155C). Over color: Light reddish-purple (RHS N78D) at the base and very light purple (RHS 76B) with light reddish-purple stripes (RHS N78D). Number of spots, dots, and stripes on the petals (upper surface): Very many flecks. Color of spots, dots, and stripes on the petals (upper surface): Reddish-purple (RHS N78A). Density of netting of the petals (upper surface): Low. Color of the netting (upper surface): Reddish-purple (RHS N78B).

*Dorsal sepal*.—Shape: Elliptic. Apex: Obtuse symmetric. Margin: Entire. Length (from base to tip): 42.0 mm to 44.0 mm. Width: 24.0 mm to 26.0 mm. Position of the broadest part of the dorsal sepals: At the middle. Color (when fully opened): Upper surface: Basic color: Light purple (RHS 76A). Over color: Reddish-purple flecks (RHS N78A) and stripes (RHS N79C). Lower surface: Basic color: Light reddish-purple (RHS N78D). Over color: Light purple shade (RHS N78B) toward the edge. Number of spots, dots, and stripes on the dorsal sepals (upper surface): Medium flecks and few stripes. Color of spots, dots, and stripes on the dorsal sepals (upper surface): Flecks RHS N78A and stripes RHS N79C. Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 40.0 mm to 42.0 mm. Width: 22.0 mm to 24.0 mm. Position of the broadest part of the lateral sepals: Toward the base. Color (when fully opened): Upper surface: Basic color: Purplish-pink (RHS N78C). Over color: Touch of light yellow-green (RHS 145D) at the base; reddish-purple flecks (RHS N78A). Lower surface: Basic color: Light reddish-purple (RHS N78D). Over color: Reddish-purple midvein (RHS N78B). Number of spots, dots, and stripes on the lateral sepals (upper surface): Many flecks. Color of spots, dots, and stripes on the lateral sepals (upper surface): RHS N78B. Density of netting of the lateral sepals (upper surface): None. Color of the netting (upper surface): Not applicable.

*Labellum* (*lip*).—Whiskers: Present. Length of whiskers: 4.0 mm to 5.0 mm. Color of whiskers: Very light purple (RHS 76B) with reddish-purple stripes (RHS N78B). Pubescence on the lip: Absent.

*Lateral lobe*.—Not applicable.

*Apical lobe*.—Shape: Extra-large lip (so-called big lip). Margin: Entire. Length: 34.0 mm to 36.0 mm. Width: 47.0 mm to 49.0 mm. Color: Upper surface: White (RHS NN155C) and flecked (RHS N79C) at the base and toward wings; purplish-pink (RHS N78C), striped RHS N78A and netted RHS N78B toward whiskers. Lower surface: White margins (RHS NN155C) from base toward margins; light reddish-purple (RHS N78D) and striped RHS N78B toward tips and whiskers. Number of spots and stripes on the apical lobe: Few flecks and medium stripes Color of spots and stripes on the apical lobe: Flecks RHS N79C and stripes RHS N78A. Density of netting of the apical lobe: High. Color of the netting: RHS N78B. Bump and ridge: Absent.

*Callus*.—Average size: Small to medium. Length: 6.0 mm to 7.0 mm. Width: 2.0 mm to 3:0 mm. Color: White (RHS NN155C) at the base; very light purple (RHS 76B) toward the tip; flecked RHS N79C.

Reproductive organs:

*Column*.—Length: 9.0 mm to 10.0 mm. Diameter: 5.0 mm to 6.0 mm. Color: Purplish-pink (RHS N78C) with two reddish-purple stripes (RHS N78A).

*Pollinia*.—Quantity: 2. Diameter: 0.8 mm to 0.9 mm. Color: Yellow-orange (RHS 23A).

*Ovary*.—Length: 10.0 mm to 12.0 mm. Diameter: 2.2 mm to 2.5 mm.

*Pedicel*.—Length: 36.0 mm to 38.0 mm. Diameter: 2.6 mm to 2.9 mm. Color: Dark purple (RHS N77A) at the base; light yellow-green (RHS 145D); purplish-pink (RHS N78C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA882884' differs from the female parent. plant '06240-0002' (unpatented) in that 'PHA882884' has short whiskers, very many flecks on the petals, but no stripes, and so-called 'Big lip' apical lobes, whereas '06240-0002' has much longer whiskers, no flecks on the petals, but medium stripes, and triangular apical lobes.

'PHA882884' differs from the male parent plant '07-1-9269'(unpatented) in that 'PHA882884' has very many flecks on the petals, and the curvature of longitudinal axis is straight, whereas '07-1-9269' has medium to many flecks on the petals, and the curvature of longitudinal axis is recurving.

'PHA882884' is most similar to the commercial *Phalaenopsis* plants named 'PHA632612' (U.S. Plant Pat. No. 35,476) and 'PHALCHORBE' (U.S. Plant Pat. No. 33,261). 'PHA882884' differs from the commercial variety 'PHA632612' in that 'PHA882884' has short whiskers that are very light purple with reddish-purple stripes, so-called 'Big lip' apical lobes with medium stripes, and purplish-pink apical lobes, whereas 'PHA632612' has very long whiskers that are purple-red with yellow tips, triangular apical lobes with no stripes, and reddish-purple apical lobes.

'PHA882884' differs from the commercial variety 'PHALCHORBE' in that 'PHA882884' has short whiskers that are very light purple with reddish-purple stripes, so-called 'Big lip' apical lobes with medium stripes, and purplish-pink apical lobes, whereas 'PHALCHORBE' has long whiskers that are white with light yellow tips, triangular apical lobes with no stripes, and white apical lobes.

I claim:

1. A new and distinct variety of *Phalaenopsis* plant named 'PHA882884', substantially as described and illustrated herein.

* * * * *